(12) United States Patent
Huet et al.

(10) Patent No.: US 8,262,615 B2
(45) Date of Patent: Sep. 11, 2012

(54) DEVICE FOR INJECTING A LIQUID INTO A BODY OF A PATIENT

(75) Inventors: Gildas Huet, Chantilly (FR); Eric Perouse, Paris (FR); Thomas Walter, Rueil-Malmaison (FR)

(73) Assignee: Laboratories Perouse, Ivry le Temple (FR)

( * ) Notice: Subject to any disclaimer, the term of this patent is extended or adjusted under 35 U.S.C. 154(b) by 0 days.

(21) Appl. No.: 13/055,311

(22) PCT Filed: Jul. 23, 2009

(86) PCT No.: PCT/FR2009/051480
§ 371 (c)(1),
(2), (4) Date: Apr. 6, 2011

(87) PCT Pub. No.: WO2010/010307
PCT Pub. Date: Jan. 28, 2010

(65) Prior Publication Data
US 2011/0178460 A1    Jul. 21, 2011

(30) Foreign Application Priority Data
Jul. 23, 2008    (FR) .................................... 08 55030

(51) Int. Cl.
*A61M 37/00*    (2006.01)
(52) U.S. Cl. ..................................................... 604/131
(58) Field of Classification Search ................... 604/131
See application file for complete search history.

(56) References Cited

U.S. PATENT DOCUMENTS

| 4,846,807 A | 7/1989 | Safadago |
| 2005/0049553 A1* | 3/2005 | Triplett et al. ................. 604/110 |

FOREIGN PATENT DOCUMENTS

| FR | 2 886 857 A1 | 12/2006 |
| WO | 98/52638 A2 | 11/1998 |
| WO | 2009/004205 A2 | 1/2009 |

* cited by examiner

*Primary Examiner* — Christopher D Koharski
*Assistant Examiner* — Jason Flick
(74) *Attorney, Agent, or Firm* — Sughrue Mion, PLLC

(57) ABSTRACT

The invention relates to a device (10) for injecting a liquid into a body, in particular that of a patient, of the type that comprises: a base (20) bearing an injection needle (22) that is to be inserted into the body; an injection conduit (24) connected to the needle (22); means (26) for extracting the needle (22) from the patient, including a plunger (52) mounted such that it can slide in relation to the base (20) between a needle (22) use position and a needle (22) extraction position; and means (28) for generating excess pressure in the injection conduit (24) as the needle (22) is extracted, including a flexible section (53) formed in the injection conduit (24), a cam surface (54) rigidly connected to the plunger (52), and a supporting surface rigidly connected to the base (20), in order to compress said flexible section (53) between the cam surface (54) and the supporting surface radially and perpendicularly to the needle (22) as the plunger (52) slides towards the needle (22) extraction position. The invention is characterized in that it includes means (56) for retaining the flexible section (53) substantially perpendicular to the needle (22).

16 Claims, 3 Drawing Sheets

DEVICE FOR INJECTING A LIQUID INTO A BODY OF A PATIENT

Figure 1:
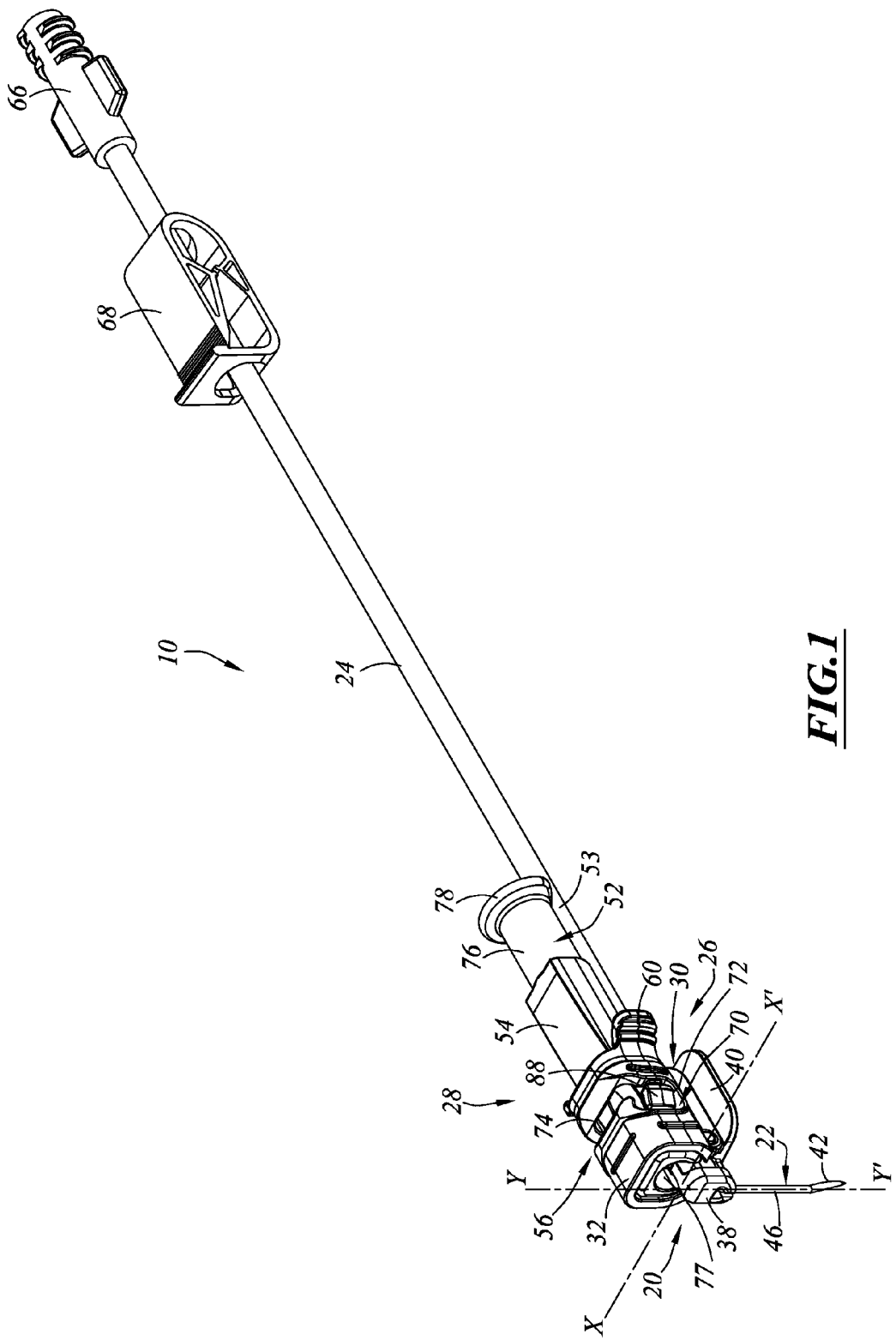

The invention concerns a device for injecting liquid into a body, such as that of a patient, of the type that comprises:
- a base bearing an injection needle that is intended to be inserted into the body;
- an injection conduit connected to the needle;
- means for extracting the needle from the patient, including a push element mounted such that it can slide in relation to the base between a needle use position and a needle extraction position;
- means for generating excess pressure in the injection conduit as the needle is being extracted, including a flexible segment formed in the injection conduit, a cam surface solidly connected to the push element and a supporting surface solidly connected to the base, in order to compress the aforementioned flexible segment between the cam surface and the supporting surface radially and perpendicularly to the needle as the push element slides towards the needle extraction position.

In certain pathologies, it is necessarily to inject a daily dose of liquid medication directly into a patient's organ. To that end, it is known to permanently implant, on the patient's chest, a chamber arranged under the skin. This chamber is extended by a catheter traveling in a vein or artery to the organ, where the drug dose must be distributed. The implantable chamber includes a reservoir having a septum that can be perforated along the contact surface of the skin.

To inject the drug dose, the needle of the device is engaged through the patient's skin in the implantable chamber and the drug dose is injected into said chamber through the needle.

To proceed with such injections, an injection device is commonly used that includes a holder integral with the needle. The holder is extended by a tube whereof one end is connected to the injection needle, and the other end of which is equipped with a connector making it possible to connect a syringe or a reservoir of a drug dose to be injected.

To remove the needle from the implantable chamber, the practitioner grasps the holder of the device and pulls the needle outside the patient.

The force deployed by the practitioner to remove the needle is relatively significant, such that the risk of sticking by rebound phenomenon is high when the needle leaves the skin. To avoid that risk, the injection device is commonly provided with an extraction assembly comprising a needle protection structure that receives the needle when it is removed to secure the needle and prevent the practitioner from being pricked.

When the needle is removed, it adheres to the septum, which rises, the inner volume of the chamber increases, thereby creating strong suction. This suction is at the catheter end that is generally located in a blood vessel. Blood then comes into the lumen of the catheter. Then, as the needle comes further out of the septum, the adhesion effect decreases, the septum then resumes its initial shape and the inner volume of the chamber decreases without reaching its initial value. A residual volume of blood then remains at the end of the catheter.

This residual volume of blood causes a deposition of fibrin (or other materials) that causes, over time, a decrease in the flow rate of the implantable chambers that can go as far as obstruction. The chamber must therefore be replaced frequently.

To offset this problem, FR 2 886 857 A1 teaches a device of the aforementioned type, in which the means for generating an over-pressure are provided in the extraction assembly to generate an over-pressure in the injection conduit during the extraction. However, with such a device, it is not easy to handle the needle during removal thereof.

The invention therefore aims to allow better handling of the needle during removal thereof.

To that end, the invention relates to an injection device of the aforementioned type, characterized in that it includes means for retaining the flexible segment substantially perpendicular to the needle.

According to other embodiments, the injection device comprises one or several of the following features, considered alone or according to all technically possible combinations:
- the transverse section of the flexible segment and the transverse section of the injection conduit have substantially the same diameter;
- the needle forms a bend;
- the retaining means can maintain the flexible segment substantially perpendicular to the plane of the needle;
- the cam surface is a face of the push element inclined relative to the direction of movement of the push element and oriented towards the bearing surface;
- the maximum value of the incline angle between the inclined face and a transverse plane of the push element is between 5° and 15°;
- the retaining means include a channel for receiving the flexible segment, formed in the base;
- the bearing surface is a flank of the receiving channel arranged substantially parallel to the direction of movement of the push element;
- the receiving channel includes an opening for inserting the flexible segment, communicating with an outer face of the base, said opening being substantially parallel to the bearing surface;
- the push element forms a cap protecting the needle, in the removal position of the needle;
- the base includes a needle holder and a sleeve, said sleeve being articulated relative to the needle holder and defining a sliding passage of the push element.

Figure 2:
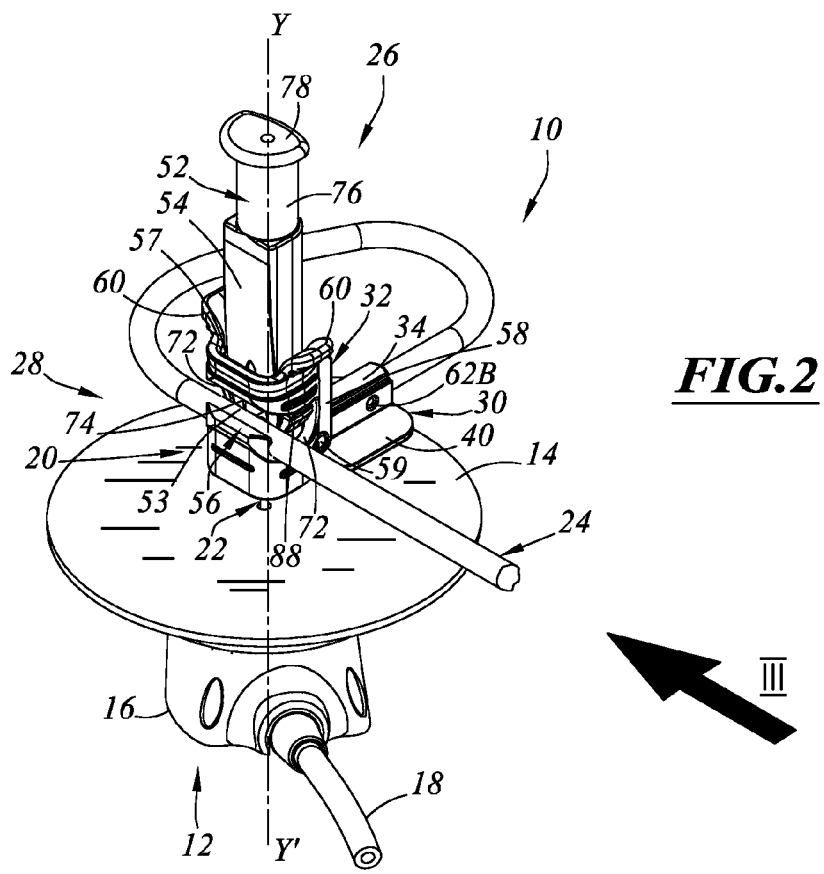
Figure 3:
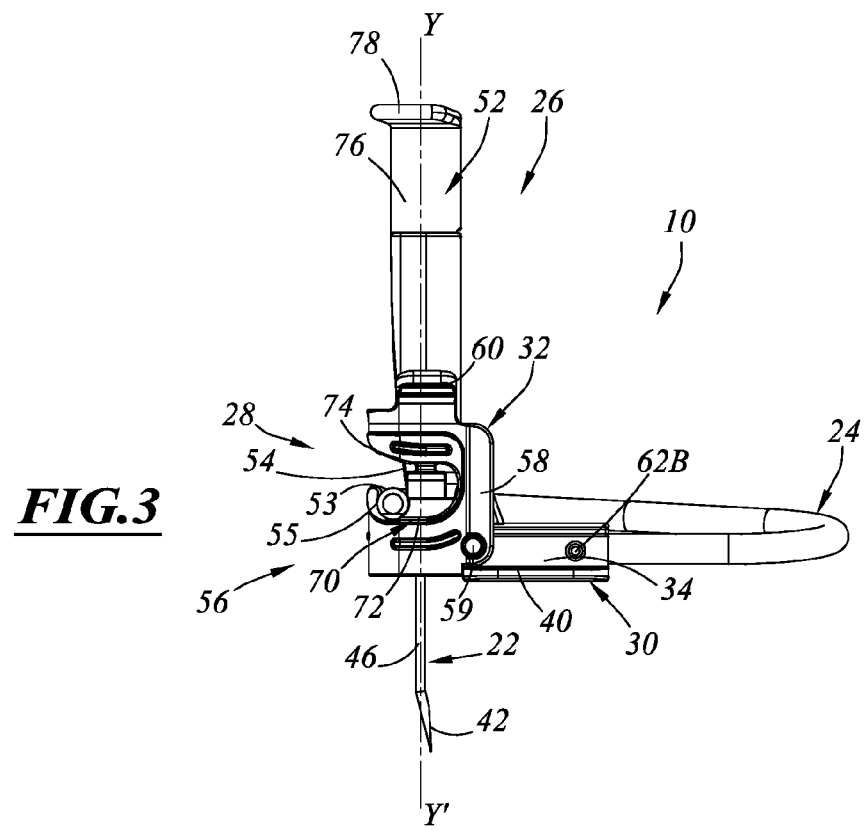
Figure 4:
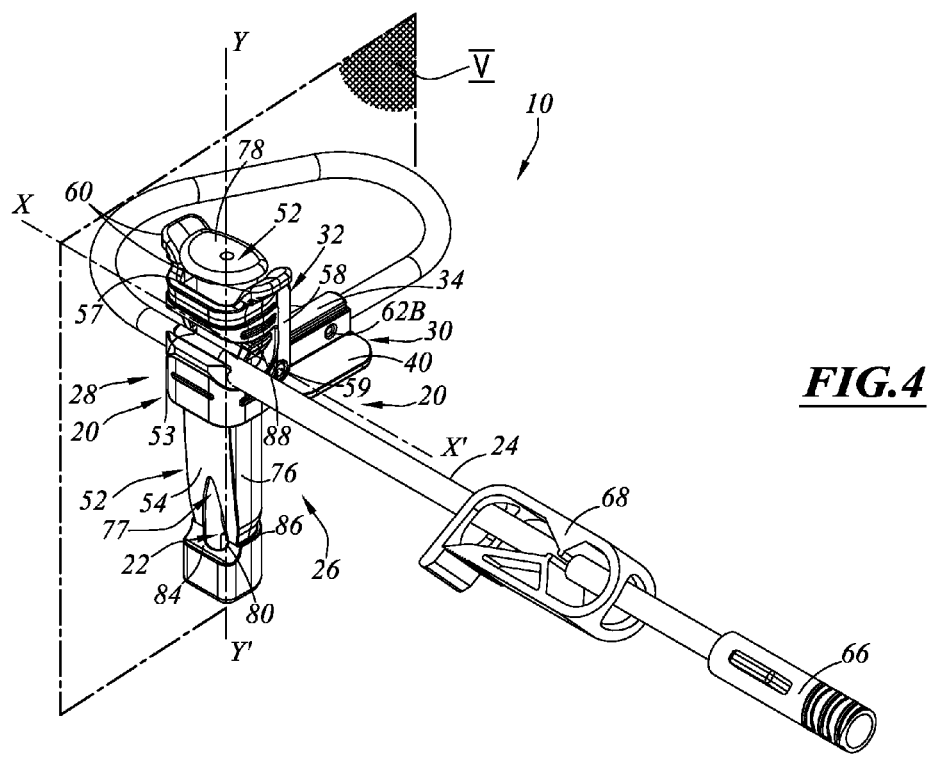
Figure 5:
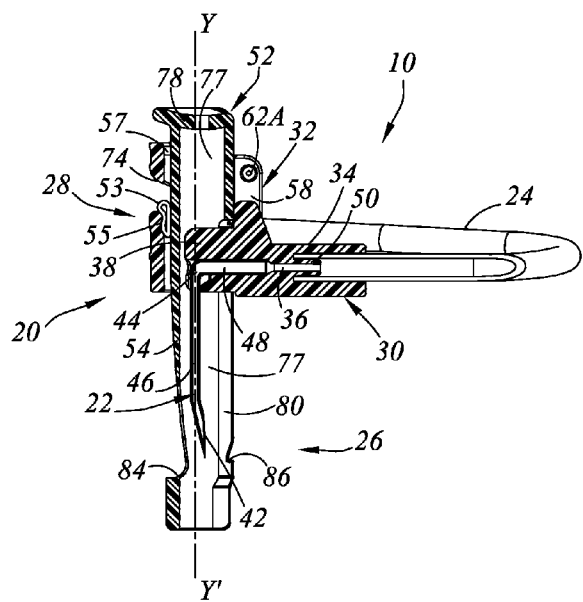

The invention and its advantages will be better understood upon reading the following description, provided solely as an example, done in reference to the appended drawings, in which:

FIG. 1 is a perspective view of an injection device in the use configuration according to the invention, FIG. 2 is a partial perspective view of the device ready to be removed from an implantable chamber, a needle of the device being engaged through the skin of a patient in the chamber, FIG. 3 is a side view of the device ready to be removed from the chamber following arrow III of FIG. 2, FIG. 4 is a perspective view of the device in the removed and secured position of the needle, and FIG. 5 is a cross-sectional view of the device along plane V of FIG. 4.

In FIG. 2, an injection device 10 is connected to an implantable chamber 12, arranged under a patient's skin 14.

The chamber 12 has a substantially cylindrical reservoir 16 defined, on its face in contact with the inner surface of the skin, by a perforable membrane, not shown. The reservoir 16 is connected to a hose 18 for conveying a drug solution towards an organ, not shown.

In FIG. 1, the injection device 10 comprises a base 20 supporting an injection needle 22, and an injection conduit 24 connected to the needle 22. The injection device 10 also includes means 26 for removing the needle from the patient and means 28 for generating an over-pressure in the injection conduit 24 during removal of the needle.

The base 20 includes a needle holder 30 and a sleeve 32 that is articulated relative to the needle holder 30.

The holder 30 includes an elongated and generally cylindrical central core 34 passed all the way through by an axial lumen 36, visible in FIG. 5, for conveying a liquid to the needle 22. The needle 22 is secured to one end, called downstream following the direction of conveyance of a liquid, of the core 34, which forms a head 38. On the side of the holder oriented towards the needle 22, the holder 30 includes a bearing plate 40 extending in the length of the support, with the exception of the end region forming the head 38 that protrudes relative to the bearing plate 40.

The needle 22 has a point-shaped curved free end 42 intended to be implanted in the patient and emerging laterally relative to the general axis of the needle. It inwardly defines a liquid injection passage.

The needle 22 forms a bend 44, visible in FIG. 5, extended on the point side 42 by a main segment 46 with a vertical axis Y-Y' and, on the side opposite the point 42, with a perpendicular connecting section 48 engaged in the axial lumen 36 from the head 38. Near the upstream end of the core 34, the lumen 36 is extended in a stud 50 ensuring the connection of the conduit 24.

The means 26 for extracting the needle from the patient comprise the base 20 and a push element 52 slidingly mounted relative to the base 20. The push element 52 can be moved between a use position of the needle 22 or an inactive position of the extraction means 26 as illustrated by FIGS. 1 to 3, and an extraction position of the needle 22 as illustrated by FIGS. 4 and 5.

The means 28 for generating an over-pressure in the injection conduit 24 during the extraction of the needle 22, comprise a flexible segment 53 formed in the injection conduit 24, a cam surface 54 integral with the push element 52 and a bearing surface 55 integral with the base 20, to compress said flexible segment 53 between the cam surface 54 and the bearing surface 55, radially and perpendicularly to the needle 22, during sliding of the push element 52 towards the extraction position of the needle 22.

The injection device 10 also includes means 56 for retaining the flexible segment 53 substantially perpendicular to the needle 22. The retaining means 56 can maintain the flexible segment 53 substantially perpendicular to the plane of the needle 22.

The sleeve 32 defines a passage 57 for circulation of a push element 52. The sleeve 32 is laterally open along a generatrix over a width corresponding to the width of the central core 34 of the holder.

On either side of said opening, the sleeve 32 is extended by two flanks 58 capable of engaging around the central core 34. For the articulation of the sleeve 32 on the central core 34, the flanks 58 are pierced with two circular holes, in which studs 59 are received integral with the central core 34 and extending along the hinge pin X-X'. The hinge pin is placed near the head 38, such that in the extraction position of the needle 22 or tilted position of the sleeve 32, the head 38 extends inside the passage 57.

At its end opposite the head 38, the sleeve 32 outwardly has two radial protuberances forming a bearing-finger 60.

The sleeve 32 has, on its flanks 58, protruding profiles 62A for elastic triggering in the complementary hollow profiles 62B of the core 34, to ensure temporary immobilization of the extraction means 26 in a folded position of the sleeve 32 on the holder 30 as illustrated by FIG. 1.

The flexible segment 53 extends between, upstream, an end 66 for connecting to a reservoir (not illustrated) of liquid to be injected, and downstream, the stud 50. The flexible tube 53 is provided, between the reservoir and the core 34, with a clip 68 capable of effectively covering the injection conduit 24 upstream of the device 10. The transverse section of the flexible segment 53 and the transverse section of the injection conduit 24 have substantially the same diameter.

The retaining means 56 include a channel 70 for receiving the flexible segment 53, formed in the sleeve 32, as shown in FIG. 3. The channel 70 extends perpendicular to the needle 22, in the direction of axis X-X'. The channel 70 includes two passage openings 72 of the flexible segment and an insertion opening 74 of the flexible segment, shown in FIG. 2. The passage openings 72 have normals substantially in the direction of axis X-X' and the insertion opening 74 is substantially perpendicular to the passage openings 72. The openings 72, 74 communicate with corresponding outer faces of the sleeve 32.

The bearing surface 55 is a flank, visible in FIG. 3, of the receiving channel 70 arranged substantially parallel to the direction of movement of the push element 52. The insertion opening 74 is substantially parallel to the flank 55.

The push element 52 is formed by a rod 76 generally hollowed out and open at one end, called front end, facing the needle 22. The rod 76 defines a cylindrical inner volume 77 for receiving the needle 22, covered at its back end by a bearing-finger 78. The rod 76 forms a cap protecting the needle 22, in the extraction position of the needle 22. The rod 76 is open, from its front end, by a slot 80 extending along the length of the push element over the main portion of the length thereof. The width of the slot 80 is sufficient to receive the central core 34.

The cam surface 54 is a face of the rod 76 inclined relative to the direction of movement of the push element 52 and oriented towards the bearing surface 55. The maximum value of the incline angle between the inclined face 54 and a transverse plane of the push element 52 is between 5° and 15°, preferably equal to 10°. The incline angle between the inclined face 54 and a transverse plane of the push element 52 varies gradually from its maximum value to 0°. The inclined face 54 is arranged on the side of the rod 76, which is opposite the slot 80. The rod 76 has, at the front end of the inclined face 54, a groove 84 for receiving the flexible segment 53 in the inactive position of the extraction means 26. The groove 84 is substantially in the direction of the channel 70 formed in the sleeve 32.

The rod 76 includes, near the groove 84, an annular outer slot 86 intended to receive elastic triggering elements 88, integral with the sleeve 32. The slot 86 and the elements 88 are capable of ensuring relative retention of the push element 52 in the inactive position of the extraction means 26.

The operation of the injection device 10 according to the invention will now be described.

Initially, during the product injection, the extraction means 26 are in their inactive position and folded along the length of the central core 34 of the needle holder, as shown in FIG. 1. To inject the drug dose, the needle 22 is engaged through the patient's skin 14 in the chamber 16 until the plate 40 bears on the patient's skin 14.

The folded extraction means 26 are then not bothersome for manipulation. Moreover, the push element 52 being folded down along the central core 34, the latter does not protrude along its entire length relative to the patient's skin 14, such that the injection device 10, after placement, can easily be maintained by an adhesive tape. The means 28 for generating an over-pressure are inactive.

To remove the injection device 10, the sleeve 32 and the push element 52 are tilted around axis X-X' to be brought into the position illustrated in FIGS. 2 and 3. The practitioner then inserts the flexible segment 53 through the insertion opening 74 in the channel 70 of the sleeve, as shown in FIG. 2. The push element 52 is placed in the axis Y-Y' of the main segment 46 of the needle, and the two extensions 60 generally extend perpendicular to the axis Y-Y'. The head 38 of the holder is received in the hollowed out push element 52.

Next, the practitioner covers the injection conduit 24 by activating the clip 68 situated upstream of the flexible segment 53. He then applies two fingers on either side of the sleeve 32 under the bearing-fingers 60 and pushes in the push element 52 using another finger, for example his thumb, bearing on the bearing-finger 78.

The front end of the push element 52 bears on the patient's skin 14, while the sleeve 32 is made to rise along the length of the push element 52. The needle 22 is thus gradually taken inside the push element 52 until it is brought into the position illustrated in FIGS. 4 and 5. In this position, the main segment 46 of the needle extends completely inside the inner volume 77 of the push element and is protected, thereby avoiding any risk of accidental sticking.

During this movement, the inclined face 54 moves towards the flexible segment 53 and perpendicular thereto. The flexible segment 53 is then gradually compressed between the inclined face 54 and the flank 55.

In the extraction position of the needle shown in FIG. 5, the portion of the flexible segment 53 arranged in the channel 70 is completely pinched between the flank 55 and the inclined plane 54.

The movement of the cam surface 54 therefore generates an over-pressure in the injection conduit 24 that causes a flow of liquid from upstream to downstream. This flow prevents blood from penetrating the hose 18 connected to the chamber 16 during extraction of the needle 22.

Thus, the flexible segment 53 is arranged in the retaining means 56 only during the extraction phase of the needle 22 from the patient, which greatly simplifies the handling of the device 10 during insertion of the needle into the chamber 16. Moreover, after insertion of the flexible segment into the retaining means 56, the flexible segment 53 is spaced away from the bearing-fingers 60 and handling of the device 10 is then facilitated during extraction of the needle 22.

The invention claimed is:

1. A device for injecting liquid into a body, such as that of a patient, comprising:
   a base bearing an injection needle that is intended to be inserted into the body;
   an injection conduit connected to the injection needle;
   an extractor for extracting the injection needle from the patient, including a push element mounted such that it can slide in relation to the base between an injection needle use position and an injection needle extraction position;
   a pressure generator for generating excess pressure in the injection conduit as the injection needle is being extracted, including a compressible and flexible segment formed in the injection conduit, a cam surface solidly connected to the push element and a supporting surface solidly connected to the base, in order to compress the aforementioned compressible and flexible segment between the cam surface and the supporting surface radially and perpendicularly to the injection needle as the push element slides towards the injection needle extraction position;
   wherein the device includes a retainer for retaining the compressible and flexible segment, substantially perpendicular to the injection needle,
   wherein the cam surface is a face of the push element inclined relative to the direction of movement of the push element and oriented towards the supporting surface, and
   wherein the maximum value of an incline angle between the inclined face and a transverse plane of the push element is between 5° and 15°.

2. The device according to claim 1, wherein the compressible and flexible segment has a transverse section, and the injection conduit has a transverse section, wherein the transverse section of the compressible and flexible segment and the transverse section of the injection conduit have substantially the same diameter.

3. The device according to claim 1, wherein the injection needle forms a bend.

4. The device according to claim 3, wherein the retainer can maintain the compressible and flexible segment substantially perpendicular to a plane of the injection needle.

5. The device according to claim 1, wherein the push element forms a cap protecting the injection needle, in the removal position of the injection needle.

6. A device for injecting liquid into a body, such as that of a patient, comprising:
   a base bearing an injection needle that is intended to be inserted into the body;
   an injection conduit connected to the injection needle;
   an extractor for extracting the injection needle from the patient, including a push element mounted such that it can slide in relation to the base between an injection needle use position and an injection needle extraction position;
   a pressure generator for generating excess pressure in the injection conduit as the injection needle is being extracted, including a compressible and flexible segment formed in the injection conduit, a cam surface solidly connected to the push element and a supported surface solidly connected to the base, in order to compress the aforementioned compressible and flexible segment between the cam surface and the supporting surface radially and perpendicularly to the injection needle as the push element slides towards the injection needle extraction position;
   wherein the device includes a retainer for retaining the compressible and flexible segment substantially perpendicular to the injection needle,
   wherein the retainer includes a receiving channel for receiving the compressible and flexible segment, formed in the base, and
   wherein the supporting surface is a flank of the receiving channel arranged substantially parallel to the direction of movement of the push element.

7. The device according to claim 6, wherein the receiving channel includes an opening for inserting the compressible and flexible segment, communicating with an outer face of the base (20), said opening (74) being substantially parallel to the supporting surface.

8. The device according to claim 6, wherein the compressible and flexible segment has a transverse section, and the injection conduit has a transverse section, wherein the transverse section of the compressible and flexible segment and the transverse section of the injection conduit have substantially the same diameter.

9. The device according to claim 6, wherein the injection needle forms a bend.

10. The device according to claim 6, wherein the retainer maintains the compressible and flexible segment substantially perpendicular to a plane of the injection needle.

11. The device according to claim 6, wherein the push element forms a cap protecting the injection needle, in the removal position of the injection needle.

12. A device for injecting liquid into a body, such as that of a patient, comprising:
- a base bearing an injection needle that is intended to be inserted into the body;
- an injection conduit connected to the injection needle;
- an extractor for extracting the injection needle from the patient, including a push element mounted such that it can slide in relation to the base between an injection needle use position and an injection needle extraction position;
- a pressure generator for generating excess pressure in the injection conduit as the injection needle is being extracted, including a compressible and flexible segment formed in the injection conduit, a cam surface solidly connected to the push element and a supporting surface solidly connected to the base, in order to compress the aforementioned compressible and flexible segment between the cam surface and the supporting surface radially and perpendicularly to the injection needle as the push element slides towards the injection needle extraction position;
- wherein the device includes a retainer for retaining the compressible and flexible segment substantially perpendicular to the injection needle, and
- wherein the base includes an injection needle holder and a sleeve, said sleeve being articulated relative to the injection needle holder and defining a sliding passage of the push element.

13. The device according to claim 12, wherein the compressible and flexible segment has a transverse section, and the injection conduit has a transverse section, wherein the transverse section of the compressible and flexible segment and the transverse section of the injection conduit have substantially the same diameter.

14. The device according to claim 12, wherein the injection needle forms a bend.

15. The device according to claim 12, wherein the retainer maintains the compressible and flexible segment substantially perpendicular to a plane of the injection needle.

16. The device according to claim 12, wherein the push element forms a cap protecting the injection needle, in the removal position of the injection needle.

* * * * *